United States Patent
Shimamoto

(10) Patent No.: US 9,993,139 B2
(45) Date of Patent: Jun. 12, 2018

(54) OPTICAL SCANNING OBSERVATION APPARATUS AND OPTICAL SCANNING OBSERVATION METHOD

(71) Applicant: OLYMPUS CORPORATION, Tokyo (JP)

(72) Inventor: Atsuyoshi Shimamoto, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days. days.

(21) Appl. No.: 15/362,192

(22) Filed: Nov. 28, 2016

(65) Prior Publication Data

US 2017/0071455 A1 Mar. 16, 2017

Related U.S. Application Data

(63) Continuation of application No. PCT/JP2015/002692, filed on May 27, 2015.

(30) Foreign Application Priority Data

May 28, 2014 (JP) ................................. 2014-110641

(51) Int. Cl.
*G02B 6/06* (2006.01)
*A61B 1/00* (2006.01)
(Continued)

(52) U.S. Cl.
CPC ...... *A61B 1/00172* (2013.01); *A61B 1/00006* (2013.01); *A61B 1/00045* (2013.01);
(Continued)

(58) Field of Classification Search
None
See application file for complete search history.

(56) References Cited

U.S. PATENT DOCUMENTS 6,856,712 B2 * 2/2005 Fauver .................. G02B 6/241
 385/12
8,212,884 B2 * 7/2012 Seibel .................. G02B 26/101
 348/206
(Continued)

FOREIGN PATENT DOCUMENTS

JP H05-137693 A 6/1993
JP 5190267 B2 4/2013
JP 2014-090780 A 5/2014

OTHER PUBLICATIONS

International Search Report dated Aug. 25, 2015 issued in PCT/JP2015/002692.
(Continued)

*Primary Examiner* — Tina Wong
(74) *Attorney, Agent, or Firm* — Scully, Scott, Murphy & Presser, P.C.

(57) ABSTRACT

An optical scanning endoscope apparatus includes an optical fiber for illumination, a driver that drives the tip of the optical fiber for illumination in a Lissajous scan pattern, illumination lenses that irradiate an object of observation with irradiation light emitted from the tip of the fiber, a photodetector that detects light obtained from the object of observation by irradiation with the irradiation light and converts the light to an electrical signal, an image processor that generates an image based on the electrical signal output by the photodetector, and a phase adjustor that adjusts the phase of the drive waveform of the driver so as to correct a phase shift between the drive waveform of the tip of the fiber by the driver and the vibration waveform of the tip of the fiber.

11 Claims, 20 Drawing Sheets

(51) Int. Cl.
  *A61B 1/05*   (2006.01)
  *A61B 1/07*   (2006.01)
  *G02B 23/24*  (2006.01)
  *G02B 26/10*  (2006.01)
  *A61B 1/06*   (2006.01)

(52) U.S. Cl.
  CPC ............ *A61B 1/00165* (2013.01); *A61B 1/05* (2013.01); *A61B 1/0638* (2013.01); *A61B 1/07* (2013.01); *G02B 23/2469* (2013.01); *G02B 26/103* (2013.01); *A61B 1/00009* (2013.01); *A61B 1/00096* (2013.01); *A61B 1/063* (2013.01)

(56) References Cited

U.S. PATENT DOCUMENTS

| | | | |
|---|---|---|---|
| 8,757,812 B2* | 6/2014 | Melville | A61B 1/0008 353/31 |
| 2013/0242069 A1* | 9/2013 | Kobayashi | A61B 1/00009 348/65 |
| 2014/0177021 A1* | 6/2014 | Shimamoto | G02B 21/0044 359/200.7 |
| 2015/0331229 A1* | 11/2015 | Nishimura | G02B 23/26 250/227.14 |

OTHER PUBLICATIONS

Japanese Office Action dated Oct. 3, 2017 in Japanese Patent Application No. 2014-110641.

* cited by examiner

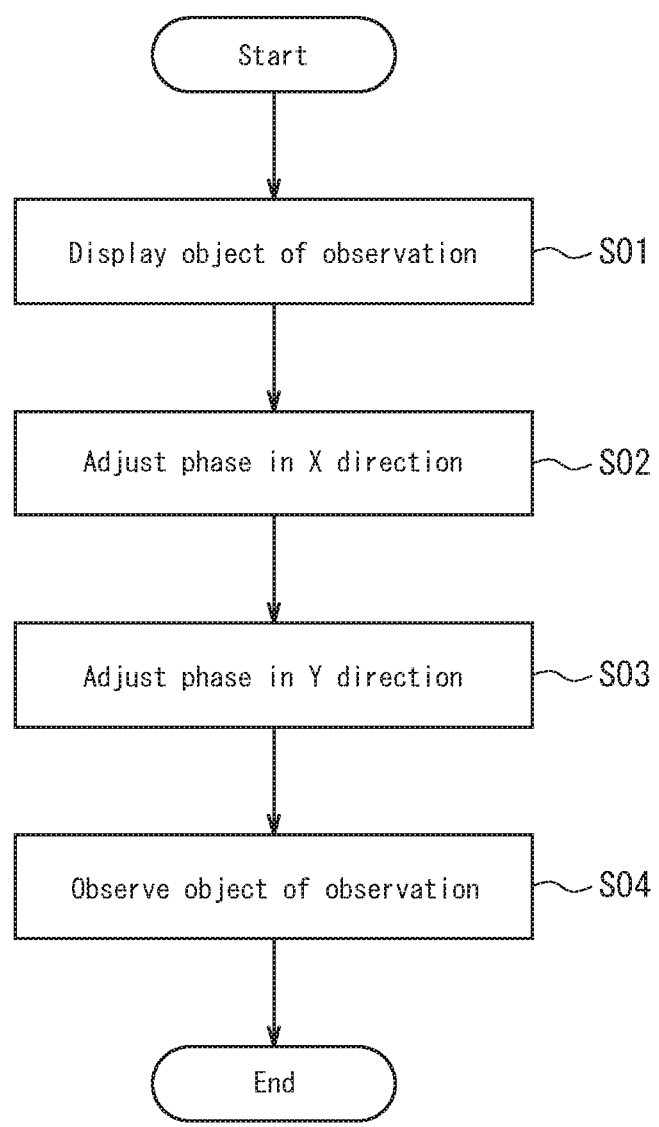

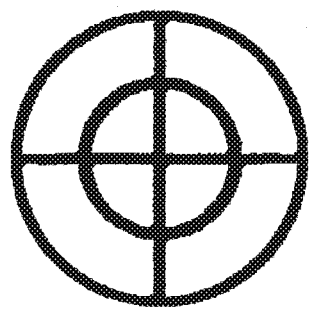
Subject
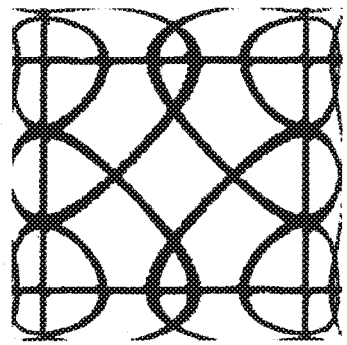
Before phase adjustment
Phase $\theta x = 0$ [deg]
Phase $\theta y = 0$ [deg]
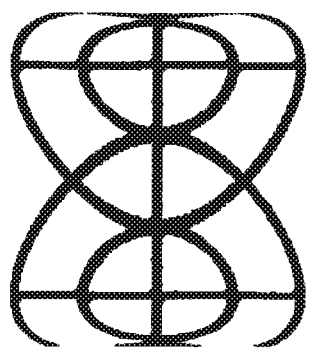
After adjustment of X phase
Phase $\theta x = 128.5$ [deg]
Phase $\theta y = 0$ [deg]
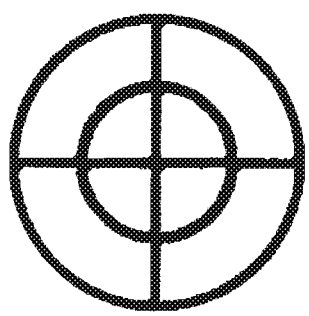
After adjustment of Y phase
Phase $\theta x = 128.5$ [deg]
Phase $\theta y = 136.8$ [deg]

Driving electrical signal (input)

Trajectory of fiber tip (input)

Subject

Display image

OPTICAL SCANNING OBSERVATION APPARATUS AND OPTICAL SCANNING OBSERVATION METHOD

CROSS-REFERENCE TO RELATED APPLICATION

The present application is a Continuing Application based on International Application PCT/JP2015/002692 filed on May 27, 2015, which in turn claims priority to Japanese Patent Application No. 2014-110641 filed on May 28, 2014, the entire disclosure of these earlier applications being incorporated herein by reference

TECHNICAL FIELD

This disclosure relates to an optical scanning observation apparatus and an optical scanning observation method for observing an object of observation with a Lissajous scan of illumination light by vibrating a fiber.

BACKGROUND

One proposed optical scanning observation apparatus is an optical scanning endoscope that holds the tip of an optical fiber for illumination to allow oscillation, scans an object of observation with illumination light by vibrating the tip, and generates an image by detecting light that is reflected, scattered, or the like, or light generated on the object of observation, such as fluorescent light (for example, see JP 5190267 B2 (PTL 1)). In such an apparatus, the object of observation is scanned with illumination light in a spiral shape (spiral scan) to acquire an image.

CITATION LIST

Patent Literature

PTL 1: JP 5190267 B2

SUMMARY

An optical scanning observation apparatus according to this disclosure comprises:
a fiber configured to guide light from a light source and supported to allow a tip of the fiber to oscillate;
a driver configured to drive the tip of the fiber in a Lissajous scan pattern by vibrating the tip of the fiber at a first frequency in a first direction and at a second frequency in a second direction, the second direction being substantially orthogonal to the first direction, and the second frequency being different from the first frequency;
an optical system configured to irradiate an object of observation with irradiation light emitted from the tip of the fiber;
a photodetector configured to detect light obtained from the object of observation by irradiation with the irradiation light and convert the light to an electrical signal;
an image processor configured to generate an image based on the electrical signal output by the photodetector; and
a phase adjustor configured to adjust a phase of a drive waveform of the tip of the fiber by the driver in one or both of the first direction and the second direction so as to correct a phase shift between the drive waveform of the tip of the fiber by the driver and a vibration waveform of the tip of the fiber.

The phase adjustor may adjust the phase of the drive waveform so as to minimize distortion of the image generated by the image processor.

The optical scanning observation apparatus may further comprise:
a display configured to display the image generated by the image processor; and
an input interface configured to receive input of an adjustment amount of the phase to be adjusted by the phase adjuster in one or both of the first direction and the second direction.

The phase adjuster may adjust the phase of the drive waveform of the tip of the fiber by the driver based on a phase of the drive waveform determined so as to maximize resolution of an image generated by the image processor for a predetermined resolution chart placed at an observation position of the object of observation.

The phase shift between the drive waveform and the vibration waveform of the tip of the fiber may be determined based on a resonance frequency and Q value of the tip of the fiber.

In this case, the optical scanning observation apparatus may further comprise a measurement unit configured to measure the resonance frequency and Q value of the tip of the fiber.

The measurement unit may measure the resonance frequency and Q value of the tip of the fiber by measuring impedance of an electric circuit of the driver.

The driver may drive the tip of the fiber in one or both of the first direction and the second direction at a frequency f satisfying $$fc\{1-1/(2Q)\} \leq f \leq fc\{1+1/(2Q)\}$$

where fc is a resonance frequency and Q is a Q value of the tip of the fiber.

An optical scanning observation method according to this disclosure is for driving a tip of a fiber in a Lissajous scan pattern by vibrating the tip of the fiber at a first frequency in a first direction and at a second frequency in a second direction, the second direction being substantially orthogonal to the first direction, and the second frequency being different from the first frequency, irradiating an object of observation with irradiation light emitted from the tip of the fiber, detecting light obtained from the object of observation by irradiation with the irradiation light, converting the light to an electrical signal, and generating an image based on the electrical signal; the method comprising:
adjusting a phase of a drive waveform of the tip of the fiber in one or both of the first direction and the second direction so as to correct a phase shift between the drive waveform of the tip of the fiber and a vibration waveform of the tip of the fiber; and
vibrating the tip of the fiber using the drive waveform with adjusted phase and observing an image.

BRIEF DESCRIPTION OF THE DRAWINGS

In the accompanying drawings:
FIG. 4A is a side view of the driver and the oscillator in the optical fiber for illumination,
and FIG. 4B is a cross-section along the A-A line in FIG. 4A;

FIG. 5 is a flowchart illustrating procedures for image observation in Embodiment 1;

FIGS. 7A, 7B, 7C, and 7D illustrate correction of image shift by adjustment of phase shift;

DETAILED DESCRIPTION

Each time a frame image is acquired in the spiral scan, the amplitude increases from zero to the maximum and then shrinks back to zero, but if the fiber is vibrated near the resonance frequency, dampening becomes slower towards the vibration center of the fiber. Therefore, an attempt to increase the frame rate causes distortion and omissions in the central part of the image. To address this issue, instead of a spiral scan, one possibility is to perform an image scan by driving the tip of the fiber in a Lissajous pattern and scanning the object of observation with illumination light using a Lissajous scan.

A Lissajous scan is a waveform obtained by combining simple harmonic motion in a first direction (for example, the X direction) and simple harmonic motion in a second direction (for example, the Y direction) orthogonal to the first direction, the two instances of simple harmonic motion having different frequencies. The ratio of the frequency in the first direction to the frequency in the second direction is an integer ratio. The drive waveform of the Lissajous scan can be represented by the following equations.

$$X = A_x \sin(2\pi f_x t)$$

$$Y = A_y \sin(2\pi f_y t)$$

At this time, the frame rate fps for example satisfies the following equations (where n is an integer).

$$f_x = (n+1) \times \text{fps}$$

$$f_y = n \times \text{fps}$$

(In the above case, $f_x > f_y$, but $f_x < f_y$ may hold instead.)

Figure 19:
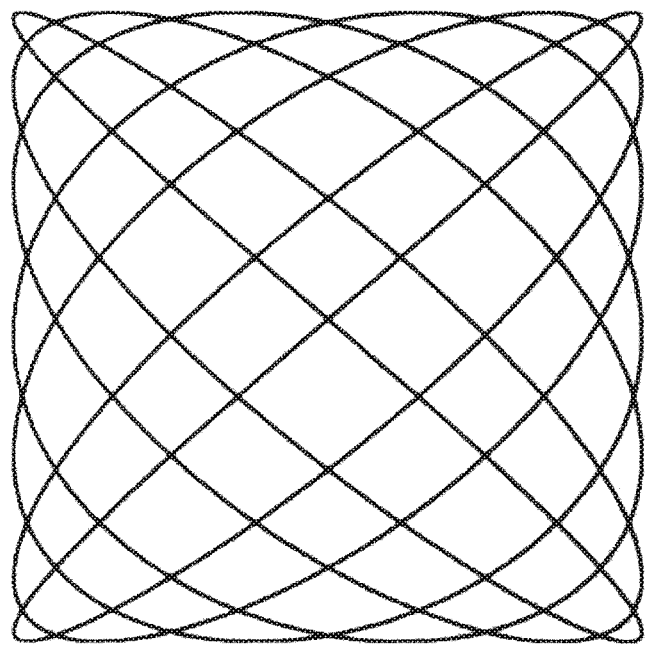
FIG. 19 illustrates an example of a Lissajous scan waveform.

FIG. 19 illustrates an example of a Lissajous scan waveform. In FIG. 19, the mesh of the scan trajectory is rough for illustrative purposes, but when used in image observation, a waveform that finely subdivides the scanning region is used, i.e. a waveform with a large integer for n. By scanning with a Lissajous pattern, the amplitude is not time modulated. Therefore, omissions and distortions do not occur in the central portion of the image as with a spiral scan, and scanning to the image center becomes possible.

Figure 20A:
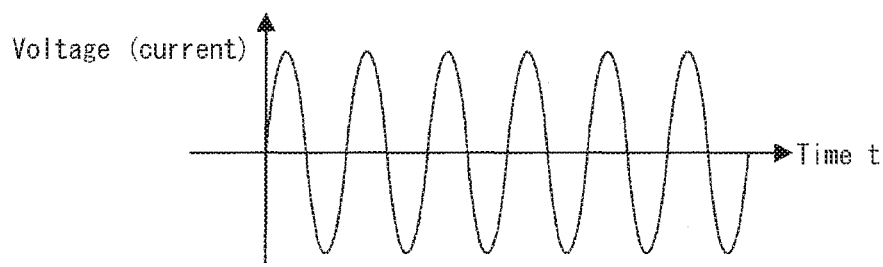
FIGS. 20A and 20B illustrate the phase shift between the driving electrical signal and the trajectory of the fiber tip, with FIG. 20A illustrating the driving electric waveform, and FIG. 20B illustrating the trajectory of the fiber tip.
Figure 20B:
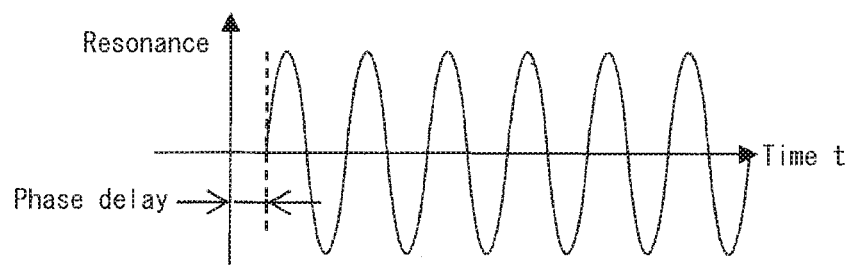

However, upon scanning with the tip of the fiber near the resonance frequency, which has high energy efficiency, phase lag occurs in the vibration waveform of the fiber tip with respect to the driving electrical signal waveform applied to the driver of the fiber. This phase lag grows larger as the driving frequency of the fiber approaches the resonance frequency. FIGS. 20A and 20B illustrate the phase shift between the driving electrical signal and the trajectory of the fiber tip, with FIG. 20A illustrating the driving electric waveform, and FIG. 20B illustrating the trajectory of the fiber tip. In an optical scanning observation apparatus using a fiber, the scan position of illumination light is calculated from the amplitude and phase of the driving signal and is stored in a lookup table, and the signals obtained from the object of observation are arranged based on the position information of the lookup table to form an image. Hence, phase shift between the driving electrical signal and the fiber tip causes misalignment and distortion in the display image.

Figure 21:
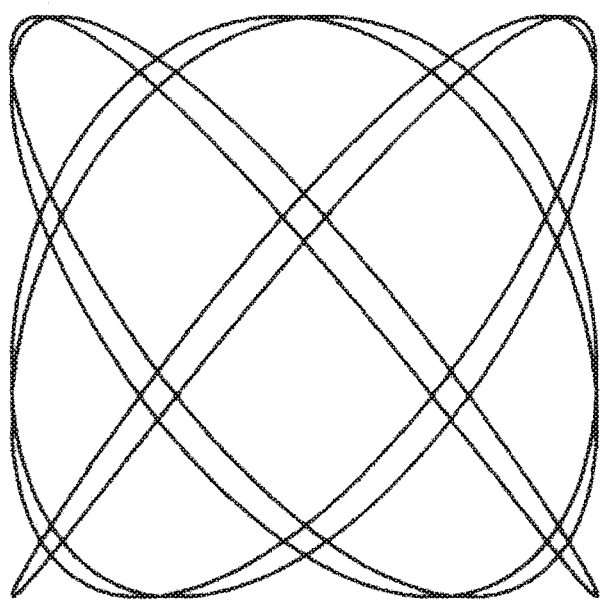
FIG. 21 illustrates distortion in the scan pattern due to phase shift.
Figure 22A:
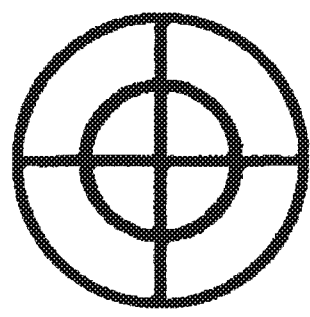
FIGS. 22A and 22B illustrate shift and distortion in the display image due to phase shift, with FIG. 22A illustrating a subject, and FIG. 22B illustrating the display image.
Figure 22B:
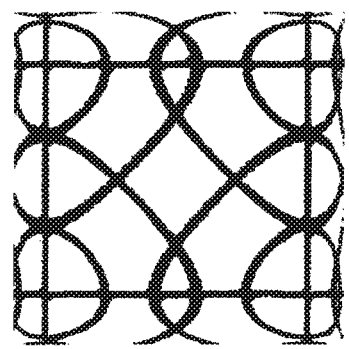

FIG. 21 illustrates distortion in the scan pattern due to phase shift. The waveform of the Lissajous pattern is shifted from the ideal waveform, and due to the distortion in the scan pattern, the subject image in FIG. 22A is observed as having the image distortion shown in the display image in FIG. 22B. Furthermore, as is clear from FIG. 21, the difference in the amount of phase shift in the X direction and the Y direction yields regions with sparse scan lines as compared to the ideal Lissajous scan. Therefore, not only does distortion occur in the image, but the resolution of the optical scanning observation apparatus also lowers. Such a reduction in resolution cannot be prevented even by correcting information on the scanning position stored in the lookup table.

Therefore, it would be helpful to provide an optical scanning observation apparatus and an optical scanning observation method that can observe an object of observation without a reduction in resolution.

Embodiments are described below with reference to the drawings.

Embodiment 1

Figure 1:
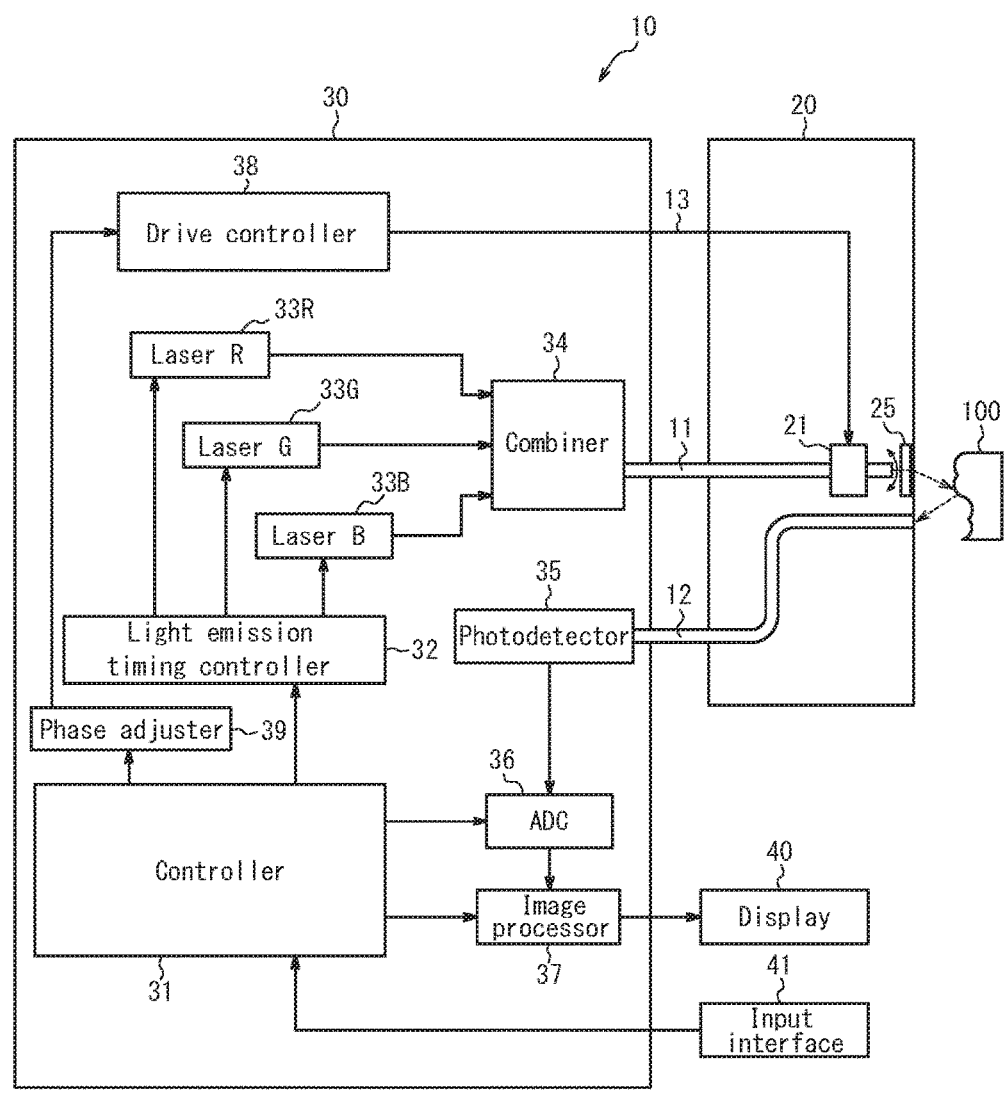
FIG. 1 is a block diagram schematically illustrating the structure of a fiber optical scanning endoscope apparatus according to Embodiment 1.

FIG. 1 is a block diagram schematically illustrating the structure of an optical scanning endoscope apparatus 10 that is an example of an optical scanning observation apparatus according to Embodiment 1. The optical scanning endoscope apparatus 10 includes a scope 20, a control device body 30, a display 40, and an input interface 41.

The control device body 30 includes a controller 31 that controls the optical scanning endoscope apparatus 10 overall, a light emission timing controller 32, lasers 33R, 33G, and 33B, and a combiner 34. Under the control of the controller 31, the light emission timing controller 32 controls the light emission timing of the three lasers 33R, 33G, and 33B that emit laser light of three primary colors, i.e. red, green, and blue. For example, Diode-Pumped Solid-State (DPSS) lasers or laser diodes may be used as the lasers 33R, 33G, and 33B. The laser light emitted from the lasers 33R, 33G, and 33B is combined by the combiner 34 and is incident as white illumination light on an optical fiber 11 for illumination (optical fiber), which is a single-mode fiber. The configuration of the light source in the optical scanning endoscope apparatus 10 is not limited to this example. A light source with one laser may be used, or a plurality of other light sources may be used. The lasers 33R, 33G, and 33B and the combiner 34 may be stored in a housing that is separate from the control device body 30.

The optical fiber 11 for illumination is led to the tip of the scope 20, and light incident on the optical fiber 11 for illumination from the combiner 34 is guided to the tip of the scope 20 and irradiated towards an object of observation 100. By a driver 21 (actuator) being subjected to vibration driving, the illumination light emitted from the optical fiber 11 for illumination can perform a 2D scan on the observation surface of the object of observation 100. The driver 21 is controlled by a drive controller 38 of the below-described control device body 30. Object light such as reflected light, scattered light, or fluorescent light that is obtained from the object of observation 100 due to irradiation with the illumination light is received at the tip of a plurality of optical fibers 12 for detection, which are constituted by multi-mode fibers, and is guided through the scope 20 to the control device body 30. Hereinafter, the optical axis direction of the tip of the optical fiber 11 for illumination is the Z direction, the directions that are orthogonal to the Z direction and orthogonal to each other are the X direction (first direction) and the Y direction (second direction), and the X direction and Y direction are the driving directions of the fiber tip.

The control device body 30 further includes a photodetector 35 for processing object light, an analog/digital converter (ADC) 36, and an image processor 37. The photodetector 35 divides the object light that passed through the optical fiber 12 for detection into spectral components and converts the spectral components into electrical signals with a photodiode or the like. The ADC 36 converts the image signal, which was converted into an analog electrical signal, to a digital signal and outputs the result to the image processor 37. Via the below-described phase adjuster 39, the controller 31 controls the ON/OFF, frequency, amplitude, phase, and the like of the driving electrical signals in the X direction and the Y direction by the drive controller 38. Furthermore, the controller 31 calculates time-series scan position information for the Lissajous scan and passes the result to the image processor 37. Alternatively, the controller 31 may store the time-series scan position information in advance as a lookup table. The image processor 37 obtains pixel data on the object of observation 100 at each scanning position from the digital signal output by the ADC 36. Furthermore, the image processor 37 sequentially stores information on the scanning position and the pixel data in a non-illustrated memory, generates an image of the object of observation 100 by performing image processing, such as interpolation, as necessary after completion of the scan or during the scan, and displays the image on the display 40.

In the above-described processing, the controller 31 synchronously controls the light emission timing controller 32, the photodetector 35, the drive controller 38 (via the phase adjuster 39), and the image processor 37.

The control device body 30 further includes the drive controller 38, phase adjuster 39, and input interface 41. The drive controller 38 includes a transmitter that generates vibration voltage in two directions: the X direction and the Y direction. The phase adjuster 39 can change the phase of the driving electrical signal by temporally shifting a timing signal, received from the controller 31, for synchronizing the phase of the driving voltage. Operations of the phase adjuster 39 and the controller 31 are executed by the CPU of the control device body 30. In FIG. 1, the controller 31 and the phase adjuster 39 are separated, but these may be implemented by the same program in the control device body 30. The input interface 41 is an input interface device, such as a keyboard or mouse, connected to the control device body 30. The user of the optical scanning endoscope apparatus 10 can perform a variety of operations with the input interface 41, such as adjusting the intensity of illumination light, expanding an image, saving and editing an image, and the like. From the input interface 41, the controller 31 also receives input of an operation to change the phase of the image being displayed, and based on this operation, the controller 31 can set the amount of phase change in the phase adjuster 39.

Figure 2:
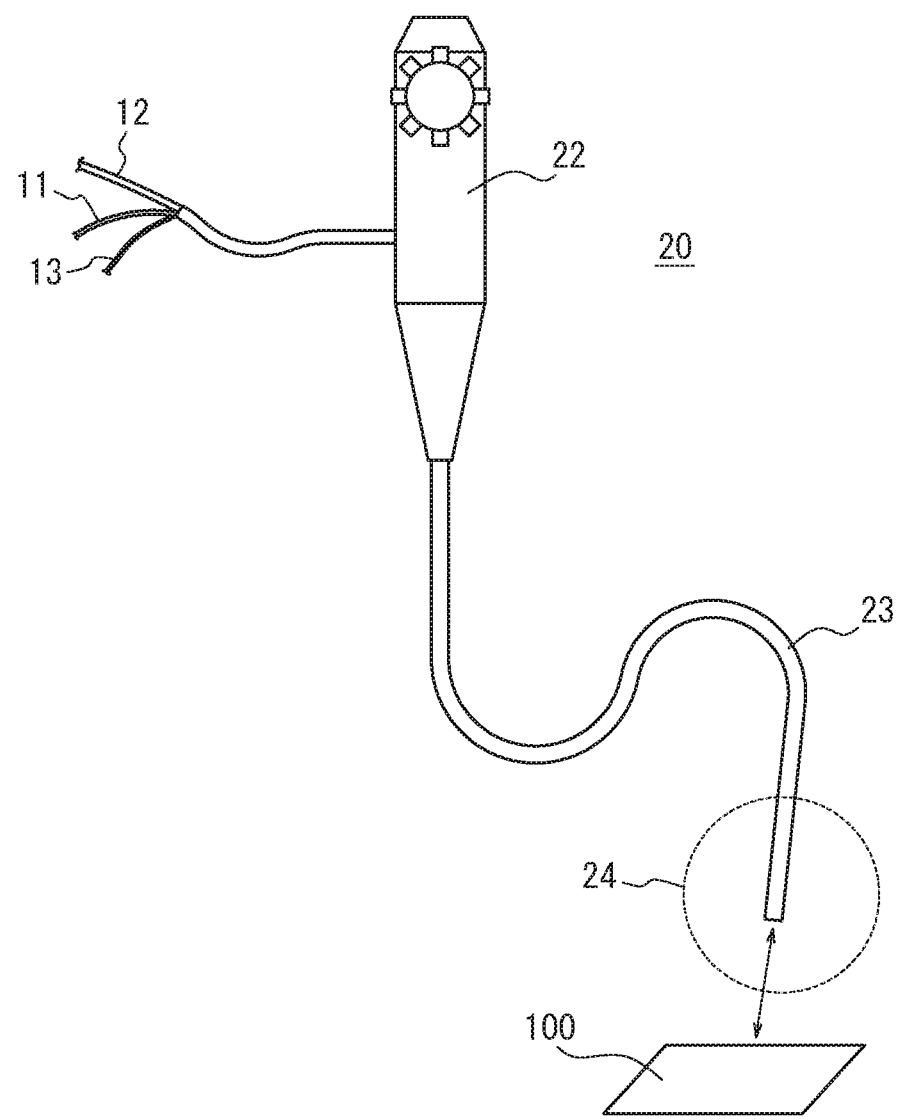
FIG. 2 is an external view schematically illustrating the scope of the optical scanning endoscope apparatus in FIG. 1.

FIG. 2 is a schematic overview of the scope 20. The scope 20 includes an operation part 22 and an insertion part 23. The optical fiber 11 for illumination, the optical fiber 12 for detection, and wiring cables 13 extending from the control device body 30 are each connected to the operation part 22. The optical fiber 11 for illumination, optical fiber 12 for detection, and wiring cable 13 pass through the insertion part 23 and are drawn to a tip 24 (the portion within the dotted line in FIG. 2) of the insertion part 23.

Figure 3:
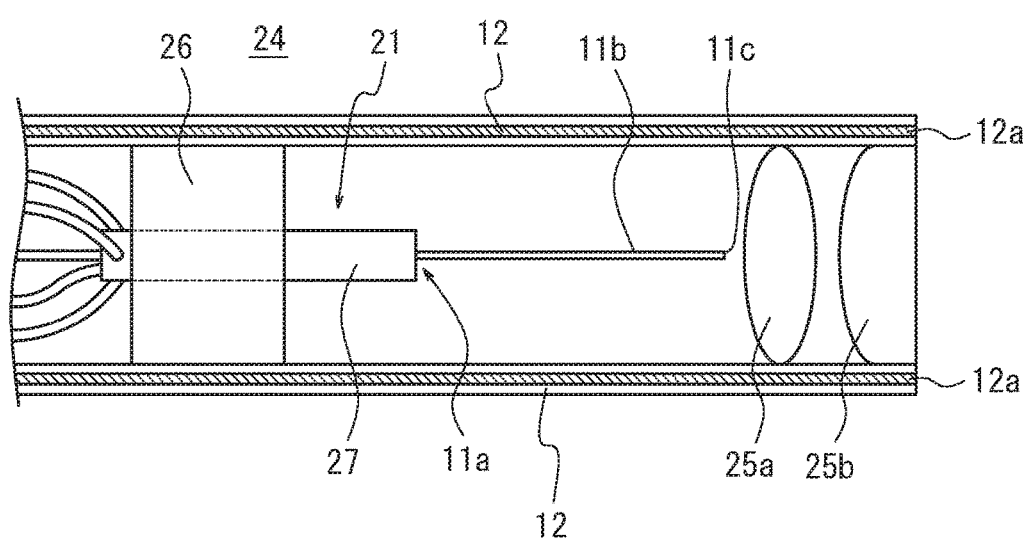
FIG. 3 is a cross-sectional diagram of the tip of the scope in FIG. 2.

FIG. 3 is a cross-sectional diagram illustrating an enlargement of the tip 24 of the insertion part 23 of the scope 20 in FIG. 2. The tip 24 includes the driver 21, illumination lenses 25a and 25b, the optical fiber 11 for illumination that passes through the central portion, and the optical fiber bundle 12 for detection that passes through the peripheral portion.

Figure 4A:
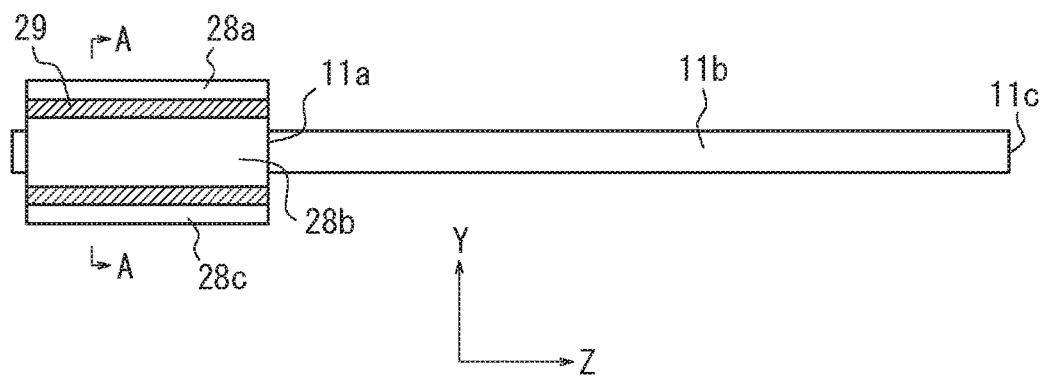
FIGS. 4A and 4B illustrate the driving vibration mechanism of the driver in the optical scanning endoscope apparatus of FIG. 1, where
Figure 4B:
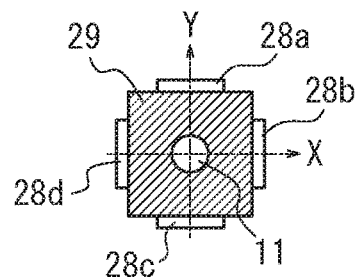

The driver 21 includes an actuator tube 27, which is fixed to the inside of the tip 24 of the insertion part 23 in the scope 20 by an attachment ring 26; a fiber holding member 29 disposed inside the actuator tube 27; and piezoelectric elements 28a to 28d (see FIGS. 4A and 4B). The optical fiber 11 for illumination is supported by the fiber holding member 29, and the portion from a fixed end 11a supported by the fiber holding member 29 to the emission end 11c is an oscillating part 1ib (tip of the fiber 11) that is supported to allow oscillation. The optical fiber 12 for detection is disposed to pass through the peripheral portion of the insertion part 23 and extends to the end of the tip 24. A non-illustrated detection lens is also provided at the tip 12a of each fiber in the optical fiber 12 for detection.

The illumination lenses 25a and 25b form an optical system that irradiates laser light emitted from the emission end 11c of the optical fiber 11 for illumination toward the object of observation 100 and are disposed so as to collect the laser light on the object of observation 100. The illumination lenses 25a and 25b are not limited to a double lens configuration and may be configured as a single lens or as three or more lenses.

A detection lens (not illustrated) is disposed so that light that is reflected, scattered, refracted, or the like by the object of observation 100 due to laser light concentrated on the object of observation 100, or fluorescent light or the like generated by irradiation with illumination light, is captured as object light, concentrated on the optical fiber 12 for detection disposed behind the detection lens, and combined.

FIGS. 4A and 4B illustrate the driving vibration mechanism of the driver 21 in the optical scanning endoscope apparatus 10 of FIG. 1, where FIG. 4A is a side view of the driver and the oscillator in the optical fiber for illumination, and FIG. 4B is a cross-section along the A-A line in FIG. 4A. The optical fiber 11 for illumination passes through the center of the fiber holding member 29, which has a prismatic shape, and is thus held by the fiber holding member 29. The four sides of the fiber holding member 29 respectively face the +Y direction, the +X direction, and the opposite −Y direction and −X direction. A pair of piezoelectric elements 28a and 28c for driving in the Y direction are fixed onto the fiber holding member 29 in the +Y direction and the −Y direction, and a pair of piezoelectric elements 28b and 28d for driving in the X direction are fixed in the +X direction and the −X direction.

The wiring cables 13 from the drive controller 38 of the control device body 30 are connected to the piezoelectric elements 28a to 28d. Voltage of equivalent magnitude and opposite sign is always applied across the piezoelectric elements 28b and 28d in the X direction. Similarly, voltage of equivalent magnitude and opposite sign is always applied across the piezoelectric elements 28a and 28c in the Y direction. One of the piezoelectric elements 28b and 28d disposed opposite each other with the fiber holding member 29 therebetween expands and the other contracts, thereby causing the fiber holding member 29 to flex. Repeating this operation produces vibration in the X direction. The same is true for vibration in the Y direction as well.

The drive controller 38 performs vibration driving of the piezoelectric elements 28b and 28d for driving in the X direction and the piezoelectric elements 28a and 28c for driving in the Y direction by applying vibration voltage of different frequencies $f_x$, $f_y$ thereto. The frequency $f_x$ is a first frequency, and the frequency $f_y$ is a second frequency. As a result, the oscillating part 11b of the optical fiber 11 for illumination vibrates, causing the emission end 11c to perform a scan. When the frequencies $f_x$, $f_y$ are near a resonance frequency fc of the oscillating part 11b of the optical fiber 11 for illumination, however, in particular when the Q value of the vibration of the optical fiber 11 for illumination is Q, and at least one of $f_x$ and $f_y$ is within the range of a frequency f satisfying the following expression:

$$fc\{1-1/(2Q)\}<f<fc\{1+1/(2Q)\},$$

then in the vibration of the emission end 11c, the phase lag from the drive waveform of the piezoelectric elements 28a to 28d increases. If such a phase lag is not adjusted, the resulting image of the object of observation 100 becomes a coarse image with a large shift or distortion.

Next, the method of adjusting phase shift in the optical scanning endoscope apparatus according to this embodiment is described. FIG. 5 is a flowchart illustrating procedures for image observation in Embodiment 1. First, the user of the optical scanning endoscope apparatus 10 selects an image with a change in the observational field of view as an object of observation and causes the object of observation to be displayed (step S01). At this time, the controller 31 drives the drive controller 38 via the phase adjuster 39, applies vibration voltage for a Lissajous scan to the driver 21, and scans illumination light over the object of observation. The light obtained by irradiation of the object of observation 100 is processed by the image processor 37 and displayed on the display 40 as an image. At this time, the phase adjuster 39 does not perform phase adjustment, and the driving signal in the X direction and the V direction can be expressed by the following equations.

$$X=A_x \sin(2\pi f_x t)$$

$$Y=A_y \sin(2\pi f_y t)$$

The frame rate fps for example satisfies the following equations (where n is an integer).

$$f_x=(n+1)\times \text{fps}$$

$$f_y=n\times \text{fps}$$

Next, the user adjusts the phase in the X direction while looking at the image displayed on the display 40 (step S02). Phase adjustment may be performed with the input interface 41. For example, the user may adjust the phase $\theta_x$ in the X direction with arrow keys on the keyboard. The phase $\theta_x$ is input to the phase adjuster 39 via the controller 31. The phase adjuster 39 holds the $\theta_x$ and shifts the phase of the timing signal received from the controller 31 by $\theta_x$ at a time, transmitting the result to the drive controller 38. As a result, the driving signal in the X direction generated by the drive controller 38 changes as follows.

$$X=A_x \sin(2\pi f_x t+\theta_x)$$

Figure 6A:
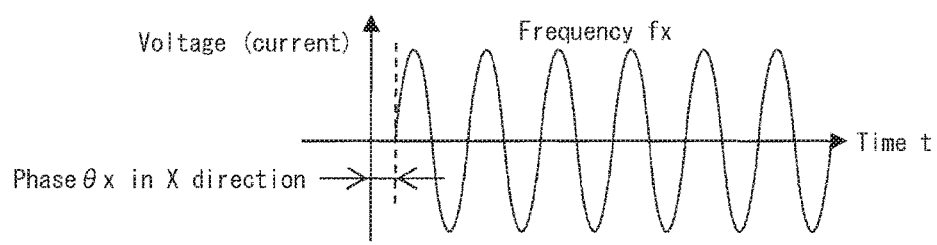
FIGS. 6A and 6B illustrate the driving signal waveform with the phase shift adjusted, with FIG. 6A illustrating the driving signal in the X direction and FIG. 6B illustrating the driving signal in the Y direction.

The driving electrical signal in the X direction at this time becomes as shown in FIG. 6A. By selecting $\theta_x$ so as to cancel out the phase shift between the driving electrical signal and the scan waveform of the fiber, the position information that the controller 31 has in the X direction for where the illumination light is irradiated in the Lissajous scan pattern and the actual position where the illumination light is irradiated match at each point in time of observation.

Next, in the same way as for adjustment in the X direction in step S02, the user adjusts the phase in the Y direction while looking at the image displayed on the display 40 (step S03). As a result, the driving signal in the Y direction generated by the drive controller 38 changes as follows.

$$Y=A_y \sin(2\pi f_y t+\theta_y)$$

Figure 6B:
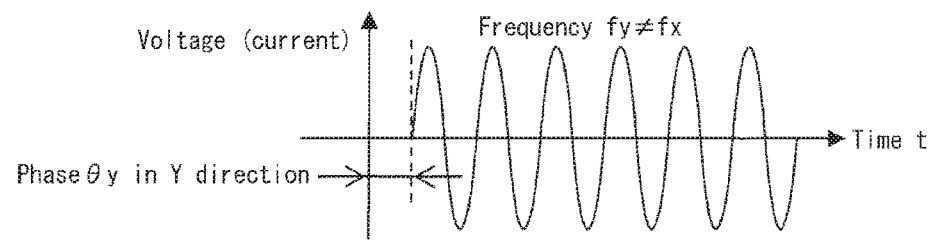

The driving electrical signal at this time becomes as shown in FIG. 6B.

With the above steps S01 to S03, the phase adjustment amounts $\theta_x$ and $\theta_y$ in the X direction and the Y direction are determined and stored in the phase adjuster 39. Therefore, in subsequent observations, the drive controller 38 can cause the emission end 11c of the optical fiber 11 for illumination to perform a Lissajous scan by driving the driver 21 with driving electrical signals that have the phase shifted by the phase adjustment amounts $\theta_x$ and $\theta_y$.

In the case of a Lissajous scan, the phase can easily be adjusted while confirming the image in this way. FIGS. 7A, 7B, 7C, and 7D illustrate correction of image shift by adjustment of phase shift. In this example, the frame rate is 15 fps, $f_x$=7545 Hz, $f_y$=7530 Hz, the resonance frequency in the X direction is 7530 Hz (which is <$f_x$), and the resonance frequency in the Y direction is 7510 Hz (which is <$f_y$). FIG. 7A illustrates the pattern of a subject that is an object of observation. Upon observing this object of observation with a Lissajous scan without adjusting the phase, an image such as the one in FIG. 7B is obtained. Deformation of this image appears as a shift in the image in the vertical or horizontal directions and as a shift in the image in the diagonal direction. Next, FIG. 7C is an image after adjusting the phase shift in the X direction. After adjustment of the X phase, only vertical shift remains. Furthermore, by adjusting the phase in the Y direction, the observation image without shift or distortion in FIG. 7D can be obtained.

As described above, according to this embodiment, the input interface 41 and the phase adjuster 39 are provided, and the phase of the drive waveforms generated by the drive controller 38 are shifted so as to correct phase shift occurring between the waveform of the driving electrical signals generated by the drive controller 38 and the vibration waveform of the emission end 11c of the optical fiber 11 for illumination. Therefore, the emission end 11c of the optical fiber 11 for illumination can be caused to perform a scan in an ideal Lissajous pattern with adjusted phase, thereby obtaining an observation image with no shift or distortion. Furthermore, the scanning pattern remains uniform, and the resolution of the observation image is not lowered.

Moreover, according to this embodiment, a position detection device, such as a Position Sensitive Detector (PSD), for detecting the scan position at each point in time need not be used, and the change over time in the scan waveform can easily be corrected. Furthermore, it is not necessary to have a large memory for storing scan position information at each point in time of the scan during the scan period.

The aforementioned phase adjustment amounts $\theta_x$ and $\theta_y$ were described as being input while the user of the optical scanning endoscope apparatus 10 looks at the image, but instead the optical scanning endoscope apparatus 10 may make a system determination of the phase adjustment amounts $\theta_x$ and $\theta_y$. For example, images with vertical and horizontal shifts among the images generated by the image processor 37 may be identified, and the controller 31 may select the phase adjustment amounts $\theta_x$ and $\theta_y$ so that these images overlap.

In the above embodiment, the phase shift has been described as being corrected in both the X direction and the Y direction, but for example when the driving frequency is near the resonance frequency in one direction and is far from the resonance frequency in the other direction, the phase shift occurring between the driving signal and the actual vibration waveform of the fiber tip is small in the other direction. Therefore, it suffices to correct the phase shift only in the direction for which the driving electrical signal is near the resonance frequency, (Modification 1)

Figure 8:
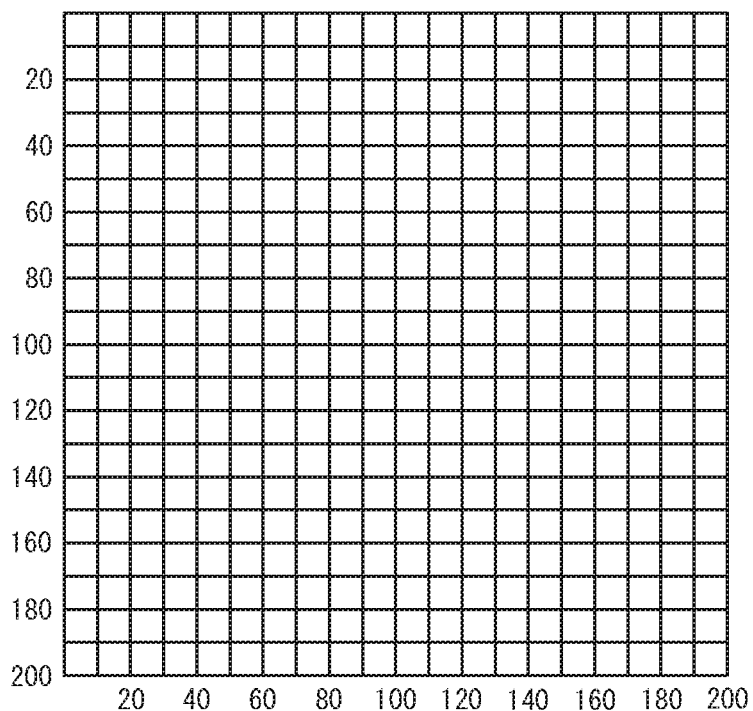
FIG. 8 illustrates an example of a correction chart according to Modification 1.

In order to calculate the phase adjustment amounts $\theta_x$ and $\theta_y$, the phase may be adjusted by preparing a special correction chart instead of using the object of observation 100. FIG. 8 illustrates an example of a correction chart. This correction chart is composed of gridlines at equal intervals. The user adjusts the phase adjustment amounts $\theta_x$ and $\theta_y$ so that the image becomes a grid when observing the correction chart. Alternatively, the shift or distortion between the gridlines and the observed image generated by the image processor 37 may be quantified, and the controller 31 may determine the phase adjustment amounts $\theta_x$ and $\theta_y$ that minimize the amount of shift or distortion.

(Modification 2)

Figure 9:
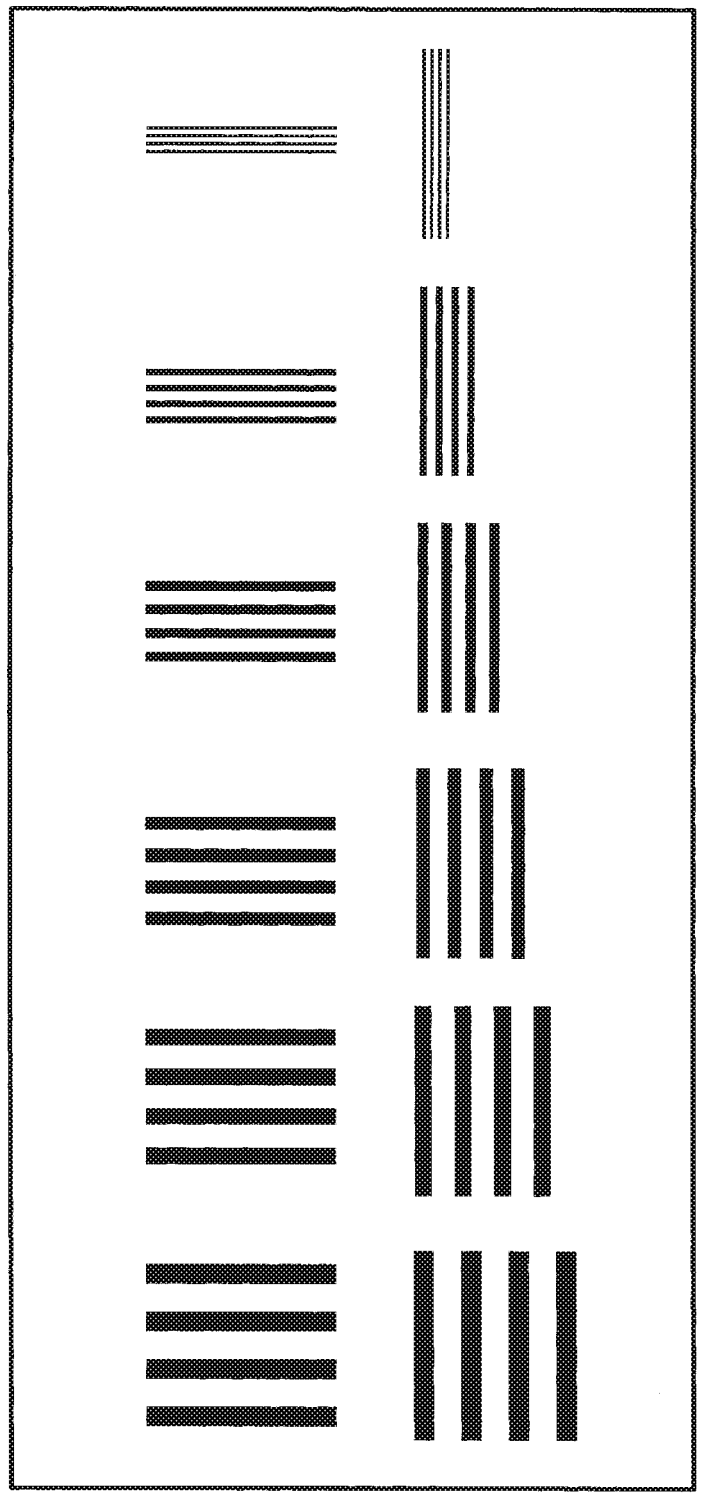
FIG. 9 illustrates an example of a resolution chart according to Modification 2.

Upon selecting the phase adjustment amounts $\theta_x$ and $\theta_y$ that minimize the phase shift, the resolution of the Lissajous scan is maximized. Therefore, instead of the object of observation 100, a resolution chart such as the one illustrated in FIG. 9 may be used to measure the resolution in the X direction and the Y direction, and $\theta_x$ and $\theta_y$ may be selected so as to maximize the resolution. In the resolution chart in FIG. 9, a plurality of black-and-white stripes with different widths are aligned at different intervals, and when observing across the stripes, the degree of resolution can be determined by whether or not each stripe can be resolved. For a predetermined resolution chart, the phase adjustment amounts $\theta_x$ and $\theta_y$ may be determined automatically while measuring the resolution with a program incorporated in the controller 31.

Embodiment 2

Figure 10:
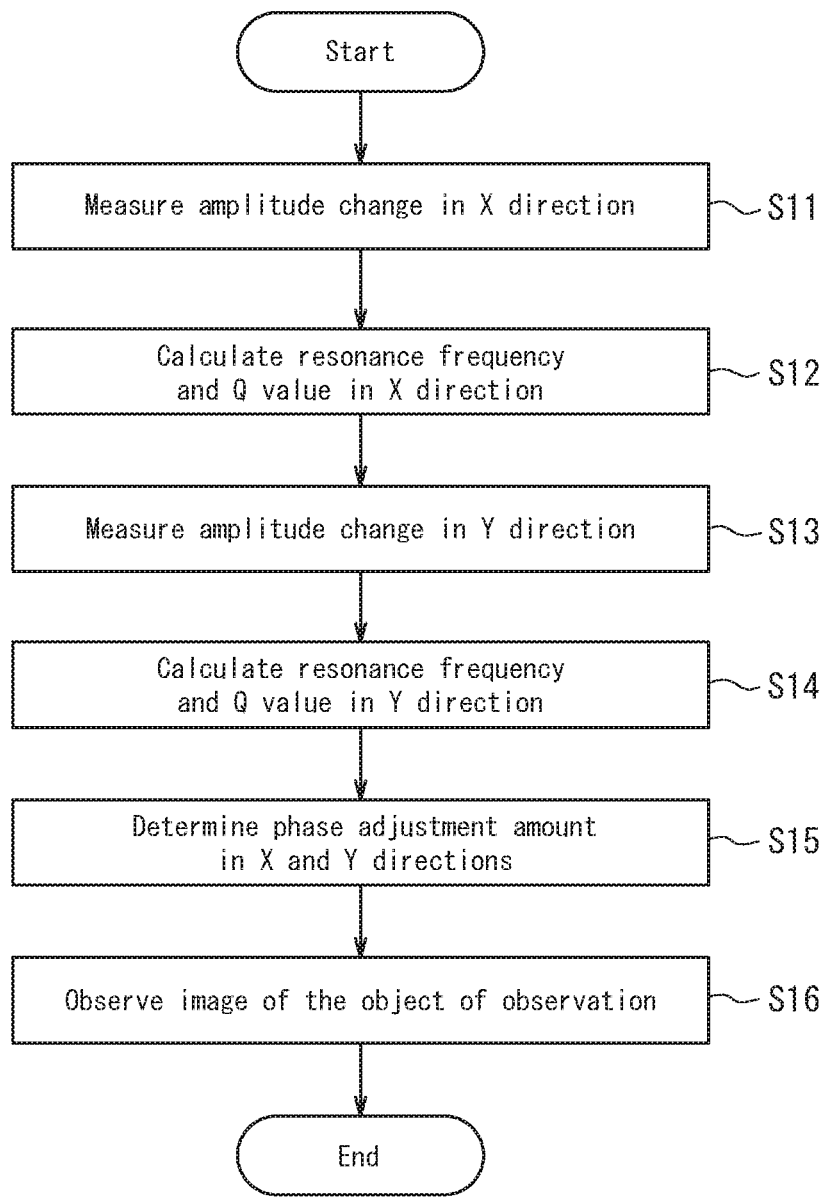
FIG. 10 is a flowchart illustrating procedures for image observation in Embodiment 2.

In Embodiment 1, in order to correct the phase shift due to a Lissajous scan near the resonance frequency, the phase adjustment amounts $\theta_x$ and $\theta_y$ are determined so as to correct the shift and distortion in the image formed by the acquired signal light. The phase shift of the optical fiber 11 for illumination with respect to the driving electrical signal, however, can be calculated by measuring the change in amplitude of the optical fiber 11 for illumination with respect to frequency and measuring the resonance frequency and the Q value. Therefore, the method for measuring the resonance frequency and the Q value using an optical scanning endoscope apparatus 10 with the same configuration as in Embodiment 1 is now described. FIG. 10 is a flowchart illustrating procedures for image observation in Embodiment 2.

First, a position sensitive detector (PSD) is placed on the plane where illumination light from the tip of the scope 20 is collected. As a result, the scanning position of the optical fiber 11 for illumination can be detected. In this state, one of the lasers 33R, 33G, and 33B is caused to oscillate, the piezoelectric elements 28b and 28d are caused to vibrate while sequentially changing the driving frequency, and the change in amplitude of the emission end 11c of the optical fiber 11 for illumination is measured in the X direction (step S11).

Figure 11:
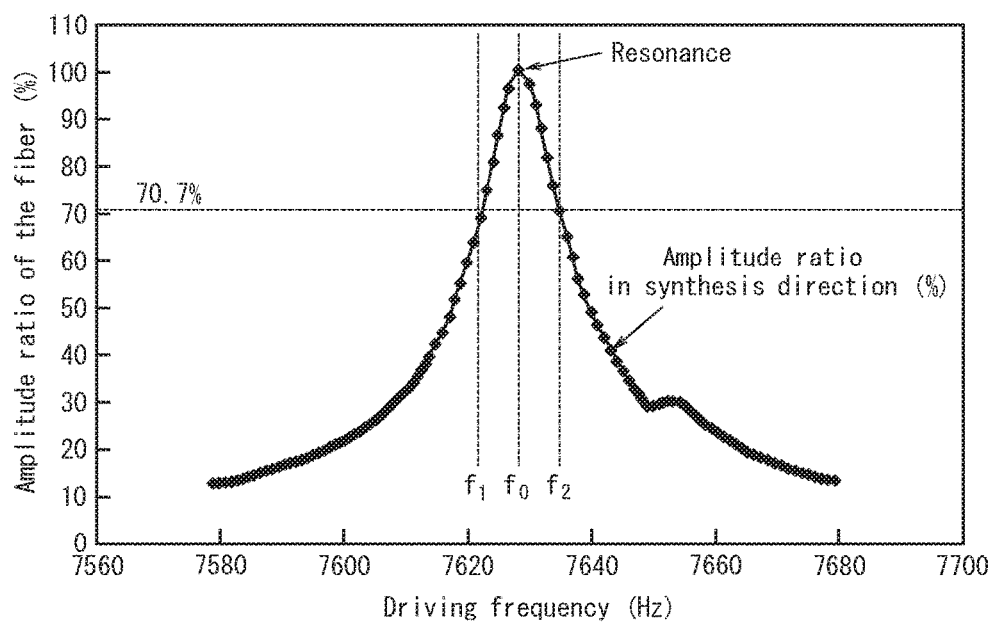
FIG. 11 illustrates a method for detecting the resonance frequency and the Q value.

Next, the resonance frequency and the Q value in the X direction of the oscillating part 11b of the optical fiber 11 for illumination are calculated (step S12). FIG. 11 is a graph of the frequency characteristics of vibration in which the amplitude ratio of the fiber is plotted along the vertical axis, with the maximum value of the fiber amplitude being 100%, and the driving frequency is plotted along the horizontal axis. In this graph, the resonance frequency $f_0$ is obtained as the driving frequency that provides the peak amplitude ratio of the fiber. The Q value is calculated from driving frequencies $f_1$ and $f_2$, for which the amplitude ratio of the fiber is approximately 70.7% (equal to $1/\sqrt{2} \times 100$), on the low frequency side and the high frequency side of the resonance frequency $f_0$.

$$Q = \frac{f_0}{f_2 - f_1}$$

After step S12, in the same way as for the X direction, the change in amplitude with respect to the driving frequency is measured near the resonance frequency in the Y direction as well (step S13), and the resonance frequency and Q value are calculated (step S14).

It is known that the resonance frequency and Q value of the fiber have a large effect on the vibration trajectory traced by the emission end 11c of the optical fiber 11 for illumination. Therefore, by changing the driving voltage, driving frequency, and phase applied to the piezoelectric elements 28a to 28d of the driver 21 based on the calculated resonance frequency and Q value, adjustments can be made so that the vibration trajectory traced by the emission end 11c of the optical fiber 11 for illumination becomes a predetermined trajectory. This principle is described below.

Figure 12:
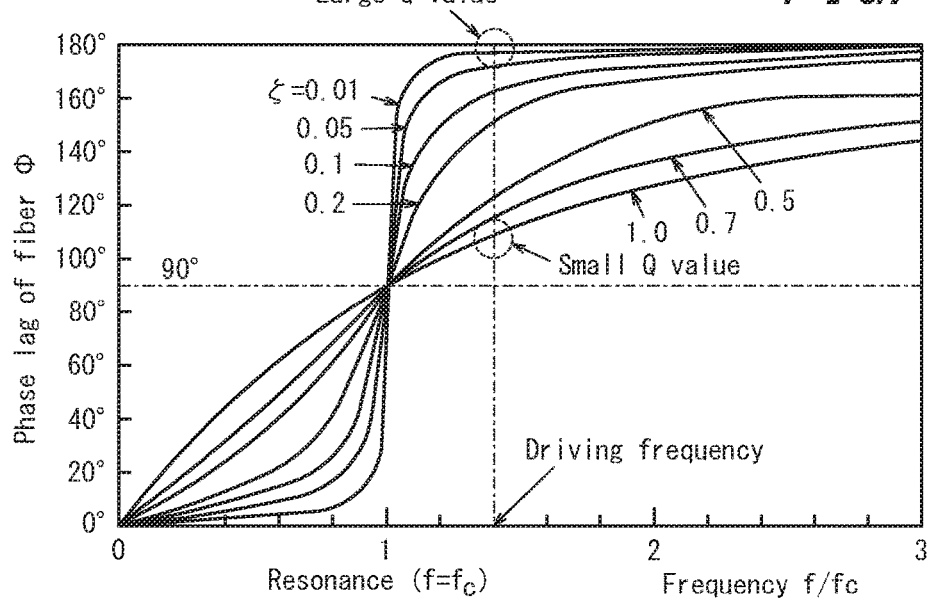
FIG. 12 illustrates the relationship between the frequency of the optical fiber and the phase lag of the fiber.
Figure 13:
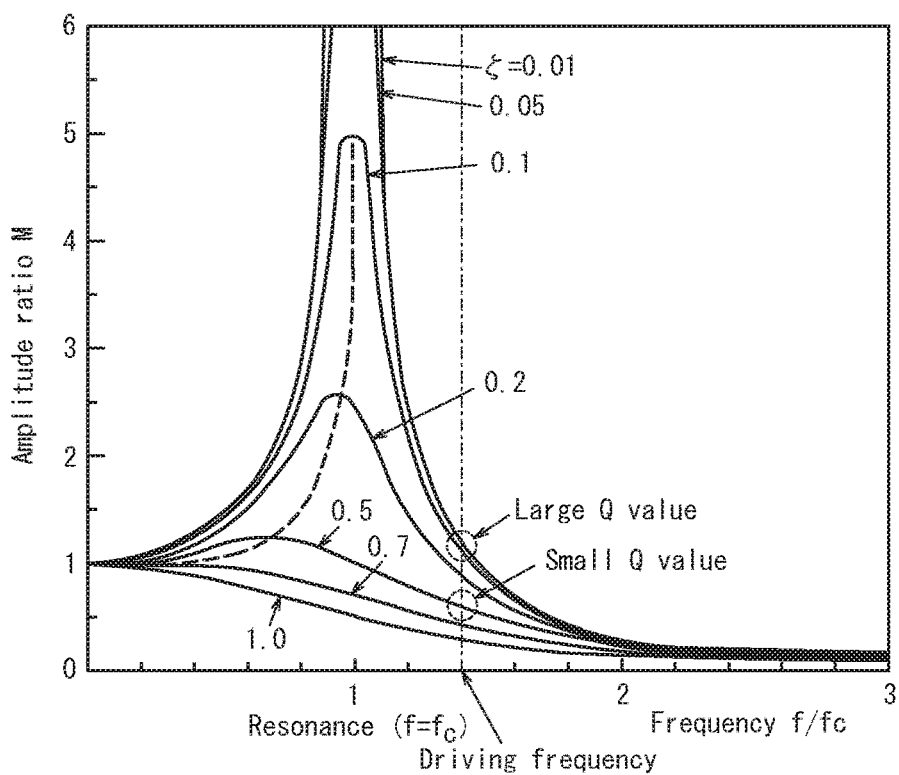
FIG. 13 illustrates the relationship between the frequency and the amplitude of the optical fiber.

FIG. 12 illustrates the relationship between the frequency of the optical fiber and the phase lag of the fiber. FIG. 13 illustrates the relationship between the frequency and the amplitude of the optical fiber. These graphs are generally known in the field of wave engineering. In FIG. 12, a plurality of curves are drawn for different values of ζ. Here, ζ is the damping ratio of the fiber vibration, and the Q value exhibits the following relationship.

$$Q = \frac{1}{2 \times \zeta}$$

In general, the Q value of the fiber vibration is an extremely large value, such that Q is approximately 50 to 300. FIG. 12 shows that upon applying vibration driving current to the driver 21, the fiber vibrates with a phase lag, but the amount of phase lag changes suddenly near the resonance frequency. Also, the change is more precipitous as the Q value is larger. FIG. 13 shows that the amplitude of the fiber increases suddenly near the resonance frequency, and as the Q value is larger, the peak amplitude is larger.

Therefore, the controller 31 calculates the phase lags in the X direction and the Y direction of the optical fiber 11 for illumination based on the calculated resonance frequency and Q value in the X direction and the Y direction and stores the phase adjustment amounts $\theta_x$ and $\theta_y$ corresponding to the phase lags in the phase adjuster 39 (step S15). After removing the PSD from the tip of the scope 20, the target object of observation 100 can be observed using the phase adjustment amounts $\theta_x$ and $\theta_y$ calculated in this way (step S16).

According to this embodiment, as in Embodiment 1, the emission end 11c of the optical fiber 11 for illumination performs a scan in an ideal Lissajous pattern with adjusted phase, thereby obtaining an observation image with no shift or distortion. Furthermore, the scanning pattern remains uniform, and the resolution of the observation image is not lowered. In addition to these effects, this embodiment allows a system determination of the phase adjustment amounts $\theta_x$ and $\theta_y$ by the optical scanning endoscope apparatus 10 itself, without user intervention for adjustment.

Embodiment 3

Figure 14:
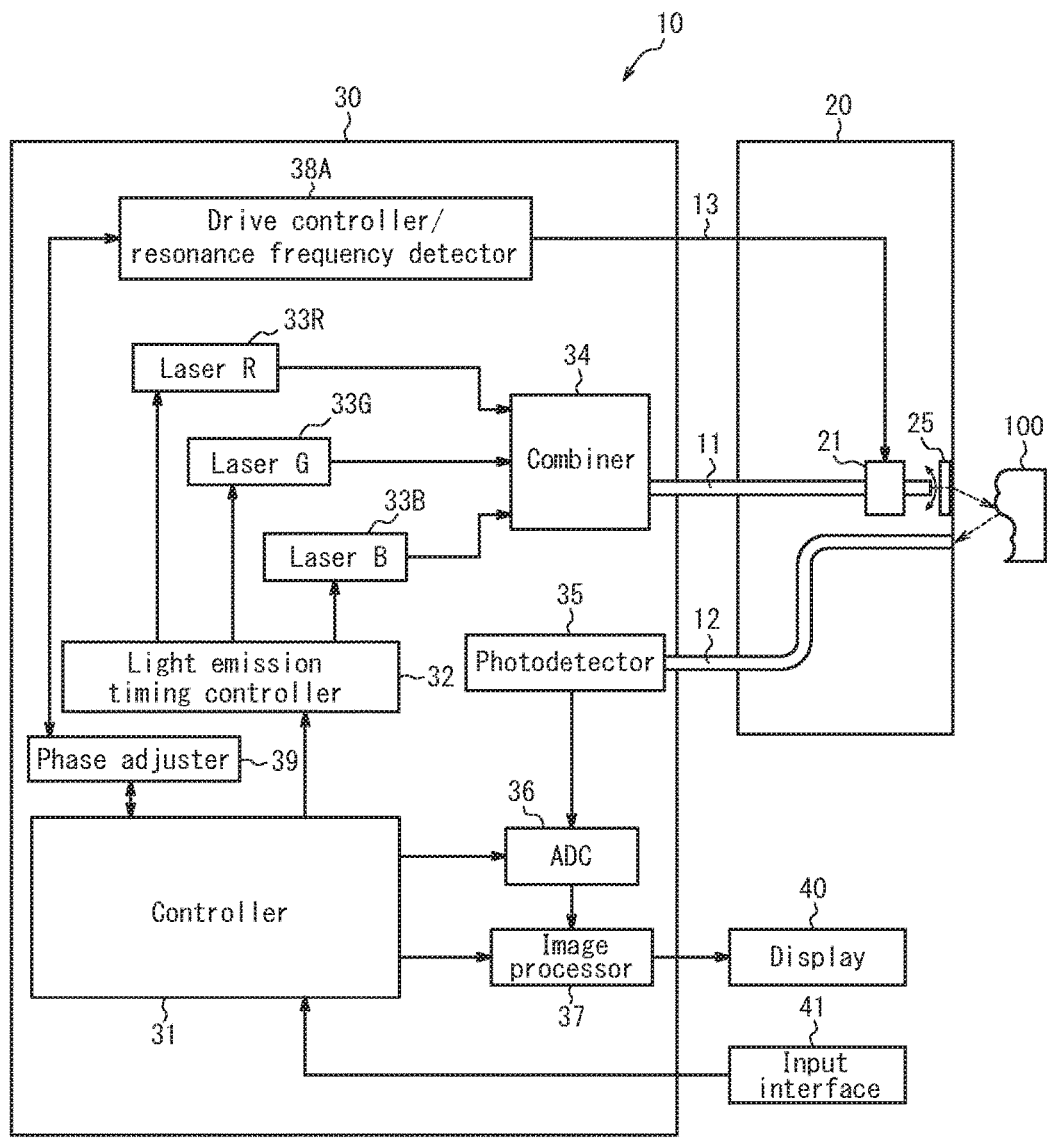
FIG. 14 is a block diagram schematically illustrating the structure of an optical scanning endoscope apparatus according to Embodiment 3.

FIG. 14 is a block diagram schematically illustrating the structure of an optical scanning endoscope apparatus according to Embodiment 3. The optical scanning endoscope apparatus according to Embodiment 3 has the configuration of the optical scanning endoscope apparatus according to Embodiment 1, except that a driver controller/resonance frequency detector 38A is provided instead of the drive controller 38. The drive controller/resonance frequency detector 38A also functions as a measurement unit that can measure the resonance frequency and the Q value of the oscillating part 11b of the optical fiber 11 for illumination.

Figure 15:
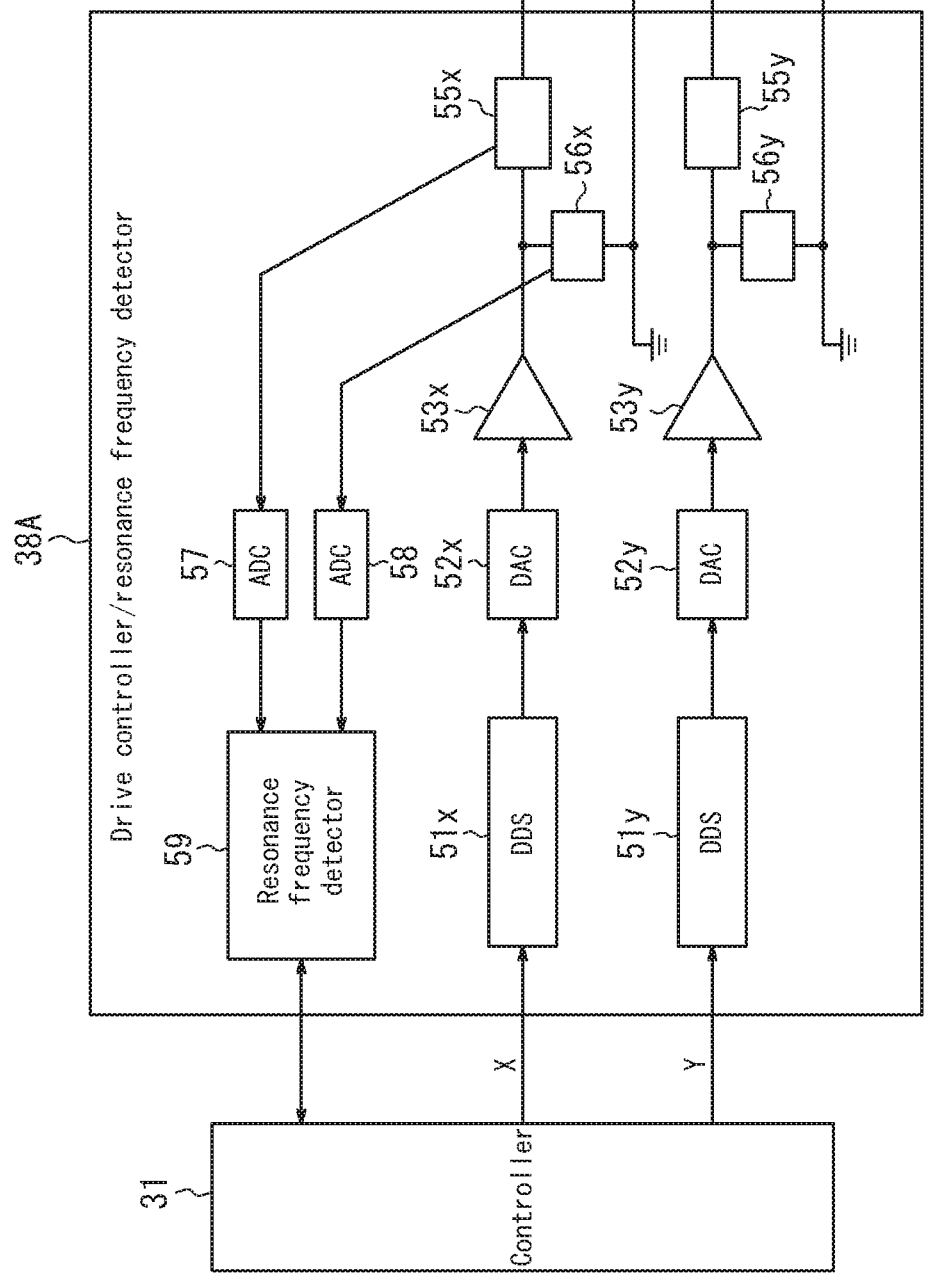
FIG. 15 is a block diagram schematically illustrating the structure of the drive controller/resonance frequency detector in FIG. 14.

FIG. 15 is a block diagram schematically illustrating the structure of the drive controller/resonance frequency detector 38A. In order to drive the piezoelectric elements 28a to 28d of the driver 21, the drive controller/resonance frequency detector 38A includes Digital Direct Synthesizers (DDSs) 51x, 51y, Digital to Analog Converters (DACs) 52x and 52y, and amplifiers 53x and 53y. The DDS 51x and DDS 51y receive respective control signals from the controller 31 and generate a digital driving signal waveform. The resulting signal is converted to an analog signal by the DACs 52x and 52y, amplified by the amplifiers 53x and 53y, and drives the piezoelectric elements 28a to 28d positioned at the tip 24 of the scope 20 via the wiring cables 13. These structural elements are almost the same as those of the drive controller 38 in Embodiment 1.

In addition to the aforementioned constituent elements, the drive controller/resonance frequency detector 38A includes a mechanism for resonance frequency detection that detects the resonance frequency of the oscillating part 11b of the optical fiber 11 for illumination. As illustrated in FIG. 15, the mechanism for resonance frequency detection includes a current detection circuit 55x and a voltage detection circuit 56x provided on the circuit from the amplifier 53x to the piezoelectric elements 28b and 28d; ADCs 57 and 58 that convert the current signal and voltage signal detected by the detection circuits to digital signals, and a resonance frequency detector 59 that detects the resonance frequency of vibration in the X direction from the phase difference between the output signals of the ADC 57 and ADC 58. In order to detect the resonance frequency of vibration in the Y direction, a current detection circuit 55y and a voltage detection circuit 56y are similarly provided, and the output of these detection circuits is also input into the resonance frequency detector 59 via ADCs (not illustrated).

In the case of detecting the resonance frequency, the controller 31 drives while gradually increasing the frequency of the driving electrical signal of the DDS 51x in the drive controller 38A. While the frequency of the driving electrical signal is increasing, the current signal and voltage signal respectively detected by the current detection circuit 55x and the voltage detection circuit 56x are monitored by the resonance frequency detector 59. By measuring the impedance via the phase shift in the current signal and voltage signal at each frequency, the resonance frequency detector 59 can detect the resonance frequency and the Q value in the X direction with a known method. The resonance frequency and Q value in the Y direction can similarly be detected.

On the other hand, the phase lag and amplitude ratio of the fiber can be calculated logically from the resonance frequency and the Q value, as illustrated in the graphs in the above-described FIGS. 12 and 13. Therefore, the controller 31 calculates the phase lag of the optical fiber 11 for illumination from the calculated resonance frequency and Q value in the X direction and the Y direction and stores the result in the phase adjuster 39. Based on the calculated amplitude ratio, the controller 31 also adjusts the amplitude in the X direction and Y direction as necessary.

In the above way, by providing the drive controller/resonance frequency detector 38A, the amount of phase adjustment can be calculated in this embodiment by a circuit without irradiating illumination light.

Accordingly, with this embodiment, even if the resonance frequency and Q value of the optical fiber 11 for illumination change, the phase adjustment amounts $\theta_x$ and $\theta_y$ can be adjusted in real time as necessary. Therefore, with this embodiment, an observation image with no shift, distortion, and reduction in resolution can be obtained, and the phase shift of the Lissajous scan can be adjusted easily. The optical scanning endoscope apparatus 10 can thus be made more convenient. This embodiment also offers the advantage of not needing to attach a PSD and perform measurements as in Embodiment 2.

Embodiment 4

Figure 16:
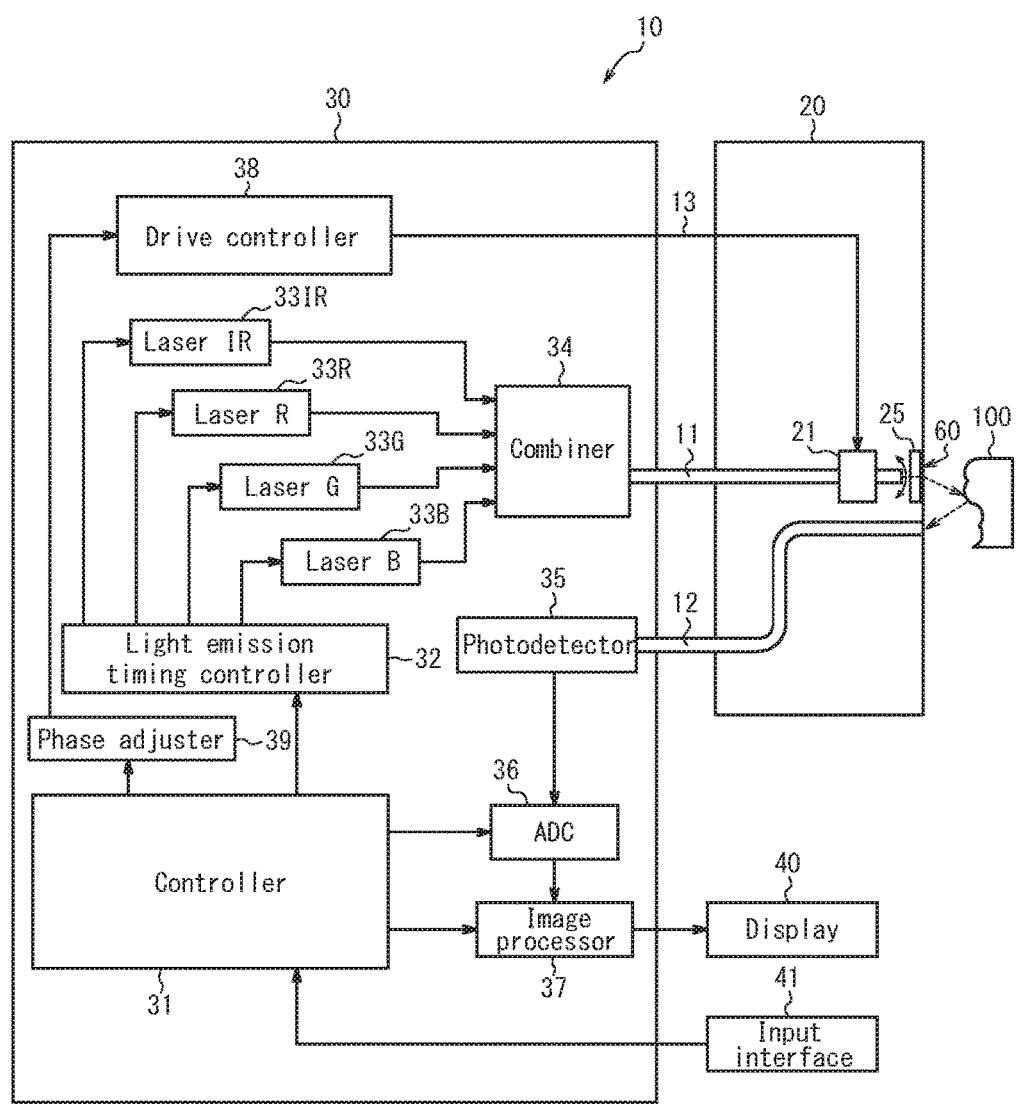
FIG. 16 is a block diagram schematically illustrating the structure of an optical scanning endoscope apparatus according to Embodiment 4.

FIG. 16 is a block diagram schematically illustrating the structure of an optical scanning endoscope apparatus according to Embodiment 4. This optical scanning endoscope apparatus has the configuration of the optical scanning endoscope apparatus according to Embodiment 1, except with the addition of a laser 33IR that emits infrared light as a light source. Like the other lasers 33R, 33G; and 33B, the laser 33IR is controlled by the light emission timing controller 32, and the output light is caused by the combiner 34 to be incident on the optical fiber 11 for illumination.

Figure 17:
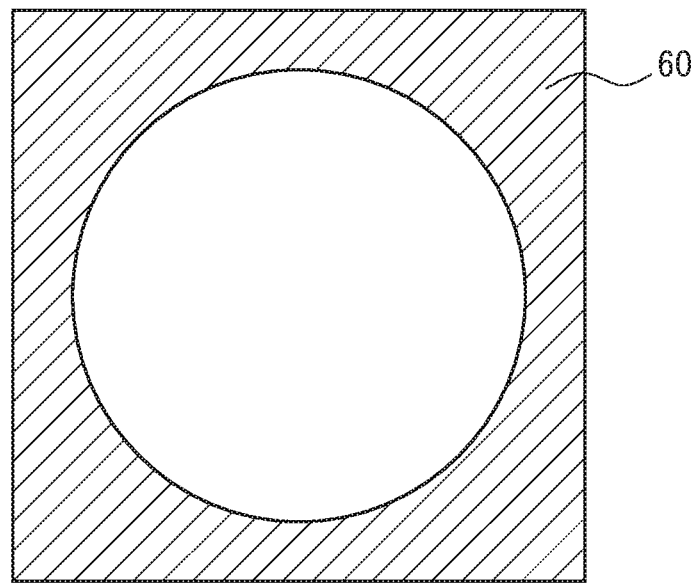
FIG. 17 illustrates an example of the light-blocking portion in FIG. 16.

A light-blocking portion 60 is provided on the surface, facing the object of observation 100, of the illumination lens 25 disposed at the tip of the scope 20. FIG. 17 illustrates the light-blocking portion 60. The light-blocking portion 60 has the characteristic of only blocking near-infrared light emitted from the laser IR while transmitting visible light. As illustrated in FIG. 17, within the rectangular area of the Lissajous scan, the illumination lens 25 is disposed so as to block light in a region excluding a circular portion in the center. The light-blocking portion is not limited to this shape and may have any of a variety of shapes.

Furthermore, the photodetector 35 is configured to separate light at the wavelength of the laser 33IR from light from the lasers 33R, 33G, and 33B and includes a detector that corresponds to the wavelength of the laser 33IR in order to detect the separated near-infrared light.

In this embodiment, in order to detect the phase adjustment amounts $\theta_x$ and $\theta_y$, the following procedure is executed.

Figure 18:
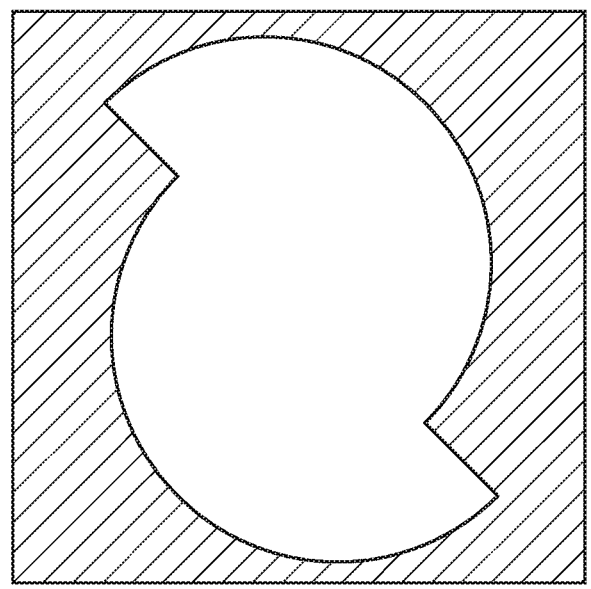
FIG. 18 illustrates an example of an image, before phase correction, that is acquired when using the light-blocking portion in FIG. 17.

First, the laser 33IR that is the near-infrared light source is caused to oscillate to acquire an image with only near-infrared light, and this image is displayed on the display 40. In the displayed image, near-infrared light is not transmitted in the portion corresponding to the light-blocking portion 60. Hence, a shadow of the light-blocking portion is formed, as illustrated in FIG. 18. The phase in the X direction and the V direction is adjusted so that the display image at the portion where light is blocked by the light-blocking portion 60 has a circular transmission region with the same shape as the light-blocking portion 60. The method of determining the phase adjustment amounts $\theta_x$ and $\theta_y$ is similar to that of Embodiment 1, and adjustment may be made while the user looks at the image, or the optical scanning endoscope apparatus 10 may make adjustments automatically.

The optical scanning endoscope apparatus 10 stores the phase adjustment amounts $\theta_x$ and $\theta_y$ determined in this way in the phase adjuster 39. At the time of image observation of the object of observation 100, the optical scanning endoscope apparatus 10 shifts the phases of the driving electrical signals of the driver 21 in accordance with these phase adjustment amounts $\theta_x$ and $\theta_y$ and uses the lasers 33R, 33G, and 33B other than the laser 33IR to irradiate the object of observation 100 and acquire an image.

Furthermore, according to this embodiment, different light sources are used for the laser 33IR for phase correction and the lasers 33R, 33G, and 33B for image observation. Therefore, while performing image observation, the laser 33IR can be turned on as necessary to correct the phase shift. Accordingly, the phase of the Lissajous scan can be corrected with increased flexibility.

This disclosure is not limited to the above embodiments, and a variety of changes and modifications may be made. For example, the optical scanning observation apparatus of this disclosure is not limited to an optical scanning endoscope apparatus and may also be adopted in an optical scanning microscope or the like. The driver is not limited to using piezoelectric elements. For example, electromagnetic driving means that uses a permanent magnet and electromagnetic coils may be used. The driving frequency, by the driver, in the X direction and the Y direction of the fiber tip may be higher or lower than the resonance frequency of the fiber tip. Alternatively, the fiber tip may be driven with a driving frequency that is higher than the resonance frequency in one direction and lower than the resonance frequency in the other direction. Furthermore, the Lissajous scan in this disclosure refers to a scanning method in which the driving frequency differs in two orthogonal directions. Accordingly, this disclosure may also be adopted with a raster scan that scans at a frequency near the resonance frequency in one direction and vibrates the fiber tip at a frequency that is significantly smaller than the resonance frequency in another direction.

The invention claimed is:

1. An optical scanning observation apparatus comprising:
a fiber configured to guide light from a light source and supported to allow a tip of the fiber to oscillate;
a driver configured to drive the tip of the fiber in a Lissajous scan pattern by vibrating the tip of the fiber at a first frequency in a first direction and at a second frequency in a second direction, the second direction being substantially orthogonal to the first direction, and the second frequency being different from the first frequency;
an optical system configured to irradiate an object of observation with irradiation light emitted from the tip of the fiber;
a photodetector configured to detect light obtained from the object of observation by irradiation with the irradiation light and convert the light to an electrical signal;
an image processor configured to generate an image based on the electrical signal output by the photodetector; and
a phase adjustor configured to adjust a phase of a drive waveform of the tip of the fiber by the driver in one or both of the first direction and the second direction so as to correct a phase shift between the drive waveform of the tip of the fiber by the driver and a vibration waveform of the tip of the fiber,
wherein the phase adjustor determines frequencies fx and fy so as to satisfy h following expressions and adjusts phases θx and θy, $X = A_x \sin(2\pi f_x t + \theta_x)$ $Y = A_y \sin(2\pi f_y t + \theta_y)$ $f_x = (n+1) \times \text{fps}$ $f_y = n \times \text{fps}$ where X is a drive waveform in the first direction, Y is a drive waveform in the second direction, $A_x$ and $A_y$ are amplitude in the first and the second direction, n is an integer, and fps is a frame rate.

2. The optical scanning observation apparatus of claim 1, wherein the phase adjustor adjusts the phase of the drive waveform so as to minimize distortion of the image generated by the image processor.

3. The optical scanning observation apparatus of claim 1, further comprising:
a display configured to display the image generated by the image processor; and an input interface configured to receive input of an adjustment amount of the phase to be adjusted by the phase adjuster in one or both of the first direction and the second direction.

4. The optical scanning observation apparatus of claim 1, wherein the phase adjuster adjusts the phase of the drive waveform of the tip of the fiber by the driver based on a phase of the drive waveform determined so as to maximize resolution of an image generated by the image processor for a predetermined resolution chart placed at an observation position of the object of observation.

5. The optical scanning observation apparatus of claim 1, wherein the phase shift between the drive waveform and the vibration waveform of the tip of the fiber is determined based on a resonance frequency and Q value of the tip of the fiber.

6. The optical scanning observation apparatus of claim 5, further comprising a measurement unit configured to measure the resonance frequency and Q value of the tip of the fiber.

7. The optical scanning observation apparatus of claim 6, wherein the measurement unit measures the resonance frequency and Q value of the tip of the fiber by measuring impedance of an electric circuit of the driver.

8. The optical scanning observation apparatus of claim 1, wherein the driver drives the tip of the fiber in one or both of the first direction and the second direction at a frequency f satisfying $$fc\{1-1/(2Q)\} < f < fc\{1+1/(2Q)\}$$

where fc is a resonance frequency and Q is a Q value of the tip of the fiber.

9. An optical scanning observation method for driving a tip of a fiber in a Lissajous scan pattern by vibrating the tip of the fiber at a first frequency in a first direction and at a second frequency in a second direction, the second direction being substantially orthogonal to the first direction, and the second frequency being different from the first frequency, irradiating an object of observation with irradiation light emitted from the tip of the fiber, detecting light obtained from the object of observation by irradiation with the irradiation light, converting the light to an electrical signal, and generating an image based on the electrical signal; the method comprising:

adjusting a phase of a drive waveform of the tip of the fiber in one or both of the first direction and the second direction so as to correct a phase shift between the drive waveform of the tip of the fiber and a vibration waveform of the tip of the fiber; and vibrating the tip of the fiber using the drive waveform with adjusted phase and observing an image, wherein adjusting the phase comprises determining frequencies fx and fy so as to satisfy the following expressions and adjusting phases θx and θy, $$X = A_x \sin(2\pi f_x t + \theta_x)$$

$$Y = A_y \sin(2\pi f_y t + \theta_y)$$

$$f_x = (n+1) \times \text{fps}$$

$$f_y = n \times \text{fps}$$

where X is a drive waveform in the first direction, Y is a drive waveform in the second direction, $A_x$ and $A_y$ are amplitudes in the first and the second direction, n is an integer, and fps is a frame rate.

10. The optical scanning observation apparatus of claim 1,
wherein the light source comprises a laser for phase correction and a laser for image observation,
wherein the optical scanning observation apparatus is provided with a light-blocking portion, between the tip of the fiber and the object of observation, which blocks only the irradiation light from the laser for phase correction and transmits the irradiation light from the laser for image observation, and
wherein the phase adjuster is configured to adjust the phase so that the image obtained by oscillating the laser for image observation has same shape as the shape of the light-blocking portion obtained by oscillating the laser for phase correction.

11. The optical scanning observation method of claim 9,
wherein the irradiation light is emitted from a laser for phase correction and a laser for image observation, and
wherein the step of adjusting the phase includes adjusting the phase so that the image obtained by oscillating the laser for image observation has same shape as the shape of the light-blocking portion obtained by oscillating the laser for phase correction.

\* \* \* \* \*